US010866243B2

(12) United States Patent
Gallagher

(10) Patent No.: US 10,866,243 B2
(45) Date of Patent: Dec. 15, 2020

(54) METHOD FOR MAKING A TEMPERATURE-INDEPENDENT PAPER TEST STRIP FOR DETECTING ZIKA VIRUS

(71) Applicant: Ashlynn Gallagher, Chehalis, WA (US)

(72) Inventor: Ashlynn Gallagher, Chehalis, WA (US)

( * ) Notice: Subject to any disclaimer, the term of this patent is extended or adjusted under 35 U.S.C. 154(b) by 220 days.

(21) Appl. No.: 16/102,981

(22) Filed: Aug. 14, 2018

(65) Prior Publication Data

US 2019/0234949 A1 Aug. 1, 2019

Related U.S. Application Data

(60) Provisional application No. 62/622,665, filed on Jan. 26, 2018.

(51) Int. Cl.

| | |
|---|---|
| ***G01N 33/577*** | (2006.01) |
| ***G01N 33/569*** | (2006.01) |
| ***D21H 19/00*** | (2006.01) |
| ***D21H 27/00*** | (2006.01) |
| ***D01C 3/00*** | (2006.01) |
| ***G01N 33/558*** | (2006.01) |

(52) U.S. Cl.

CPC ........... *G01N 33/577* (2013.01); *D21H 19/00* (2013.01); *D21H 27/00* (2013.01); *G01N 33/56983* (2013.01); *C12Y 111/01007* (2013.01); *D01C 3/00* (2013.01); *G01N 33/558* (2013.01); *G01N 2333/183* (2013.01)

(58) Field of Classification Search

None

See application file for complete search history.

(56) References Cited

PUBLICATIONS

Qi et al. International J. Molecular Sciences 2017 vol. 18, 237 (Year: 2017).*

Kaufman et al., "Visualization and Measurement of Flow in Two-dimensional Paper Networks," Lab Chip. Oct. 7, 2010; 10(19): 2614-2617.

Lu et al., "Stabilization and Release of Enzymes from Silk Films," Biomacromolecules May 11, 2009, 10(5), 1032-1042.

Rockwood et al., "Materials Fabrication from Bombyx mori Silk Fibroin," Nat Protoc. Sep. 22, 2011; 6(10): 10.1038/nprot.2011.379.

Vepari et al., "Silk as a biomaterial," Prog. Poly Sci. 2007, 32, 991-1007.

Fourcade et al., "Viral Load Kinetics of Zika Virus in Plasma, Urine and Saliva in a Couple Returning from Martinique, French West Indies," Journal of Clinical Virology, vol. 82, 1-4, 2016.

* cited by examiner

*Primary Examiner* — Changhwa J Cheu

(74) *Attorney, Agent, or Firm* — George A. Leone; Citadel Patent Law

(57) ABSTRACT

A method for making and a resultant paper test strip product for detecting Zika antibodies indicating the presence of Zika virus in a patient sample. The paper test strip includes a strip of filter paper; and a silk fibroin solution applied to the strip of filter paper wherein the silk fibroin solution is mixed with an enzyme solution in phosphate buffered saline buffer.

15 Claims, 3 Drawing Sheets

METHOD FOR MAKING A TEMPERATURE-INDEPENDENT PAPER TEST STRIP FOR DETECTING ZIKA VIRUS

TECHNICAL FIELD

The present invention relates to a method for detecting Zika Virus. More particularly, the method and apparatus are directed to a method for making a temperature-independent paper test strip for detecting Zika virus.

BACKGROUND

The Zika virus (ZIKV) is an infectious disease from the virus family Flaviviridae which is spread from the *Aedes* mosquitoes which are active during the day. Zika was originally isolated in the Zika Forest of Uganda where it was found in monkeys, and then later identified in humans in 1952 (WHO, 2017). The first major outbreak of Zika infection was found in the Island of Yap in 2007 (WHO, 2017). As stated from an article published by Science Magazine, "For nearly 7 decades, the Zika virus would remain a virological curiosity, receiving little more attention than other obscure members of the Flaviviridae family that are transmitted by mosquitoes, such as Spondweni, Wesselsbron, and Ntaya. But now that it appears Zika might be causing serious harm to babies in Brazil, the World Health Organization has deemed it a 'public health emergency of international concern.' It's fast earning the reputation of the scariest virus on the planet."

Zika virus is known to cause fever, rash, headache, and conjunctivitis, but Zika's biggest threat is to pregnant women, because the virus can pass onto the fetus. If Zika passes onto the fetus during pregnancy, the virus can cause a birth defect called microcephaly (CDC, 2017).

For most people, Zika is a very mild infection and is not harmful. An article reported by CNN, "In these areas, women who are pregnant need to protect themselves from mosquito bites by using repellents, permethrin-coated clothing, long sleeves and pants, and by staying indoors (ideally in places with air conditioning) as much as is practical. We advise pregnant women to postpone travel to areas where Zika is spreading" (CNN, 2016). Due to travel hazards, many people are canceling trips to Zika infested areas to avoid the risk of contracting the virus. However, many of the population of South America are not able to travel outside of South America to avoid contracting the virus, or are not able to use repellents, permethrin-coated clothing, etc. Some people may not be aware of special precautions whilst others are not aware that they are carrying the virus (New York Times, 2016).

IgM Antibody Capture Enzyme-Linked Immunosorbent Assay (MAC-ELISA) tests are currently one of the options for Zika detection and use an oxidation reaction caused by Horseradish peroxidase (HRP) onto 3,3'5,5'-Tetramethylbenzidine (TMB). HRP is an enzyme normally found in the roots of Horseradish, and TMB is an enzyme substrate. Initial inspiration was derived from journals about rapid HIV tests and MAC-ELISA antibody tests.

Current diagnostics for detecting Zika cost between $299 to $800 on the private market if patients do not fit the CDC's criteria (New York Times, 2016). Due to expensive prices, many pregnant women are resulting to abortions if infected, or they are deciding to not get pregnant. People must wait long periods of time to get tested if they don't meet the CDC's criteria. Many tests for Zika are complicated and take days up to weeks to get results back due to current diagnostics being lab tests. Zika tests are first come, first serve, and as stated from an article published by the New York Times, "Public health experts say the restrictions are necessary to ensure that people most at risk have access to testing. 'We aren't interested in stimulating the testing of simply anxious people,' according to an infectious diseases specialist at Vanderbilt University Medical Center. 'We want health care providers to provide the appropriate counseling and to be selective in the use of this test, as they are in the use of any other test'" (New York Times, 2016). Due to lack of resources and time, many patients infected with Zika do not know they have the virus, and many cannot be tested due to lack of resources and time. In order to combat the problem in the field, a temperature-independent, low cost, efficient, diagnostic system needs to be made.

The present invention overcomes the deficiencies of the prior art by providing a method for making a low-cost paper test strip that can be used in remote locations, disaster areas, at home, or in the field of research, it will be possible to detect Zika in a more effective and faster way.

BRIEF SUMMARY OF THE DISCLOSURE

This summary is provided to introduce, in a simplified form, a selection of concepts that are further described below in the Detailed Description. This summary is not intended to identify key features of the claimed subject matter, nor is it intended to be used as an aid in determining the scope of the claimed subject matter.

Disclosed herein is a method for making and using a resultant paper test strip product for detecting Zika antibodies indicating the presence of Zika virus in a patient sample. The paper test strip includes a strip of filter paper coated with a silk fibroin solution, wherein the silk fibroin solution is mixed with an enzyme solution in phosphate buffered saline buffer.

BRIEF DESCRIPTION OF THE DRAWINGS

While the novel features of certain embodiments of the invention are set forth with particularity in the appended claims, the invention, both as to organization and content, will be better understood and appreciated, along with other objects and features thereof, from the following detailed description taken in conjunction with the drawings, in which:

Figure 1:
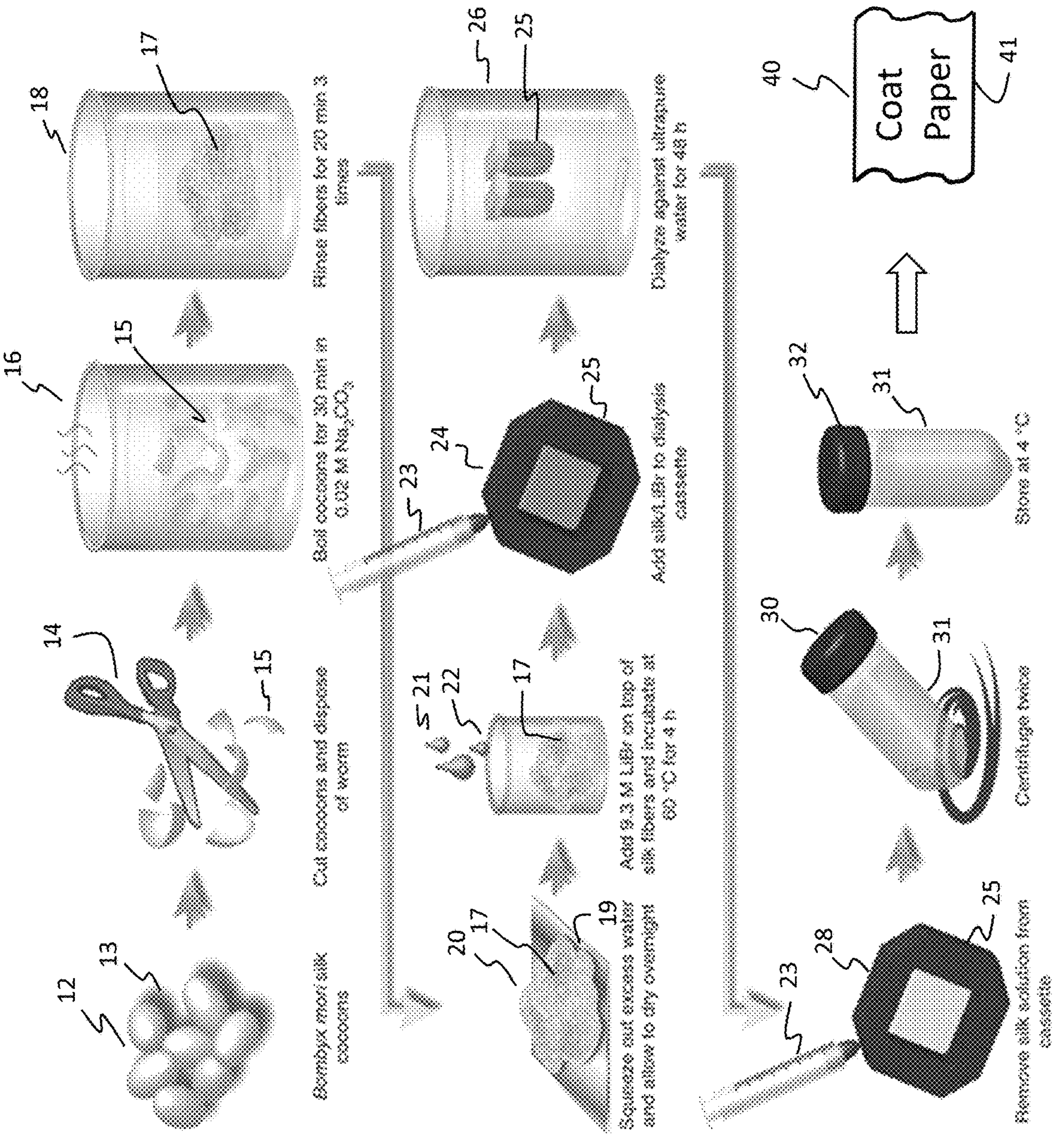
FIG. 1 schematically illustrates a process flow diagram of a silk fibroin extraction procedure for making a Zika test strip.

In the drawings, identical reference numbers identify similar elements or components. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements and have been solely selected for ease of recognition in the drawings.

DETAILED DESCRIPTION

The following disclosure describes a method for making a temperature-independent test strip for detecting Zika virus.

Several features of methods and products in accordance with example embodiments are set forth and described in the figures. It will be appreciated that methods and products in accordance with other example embodiments can include additional procedures or features different than those shown in the figures. Example embodiments are described herein with respect to a method and system directed to using silk fibroid and 2D paper networks for making the test strip. However, it will be understood that these examples are for illustrating the principles, and that the invention is not so limited.

Unless the context requires otherwise, throughout the specification and claims which follow, the word "comprise" and variations thereof, such as, "comprises" and "comprising" are to be construed in an open, inclusive sense that is as "including, but not limited to."

Reference throughout this specification to "one example," "an example embodiment," "one embodiment," "an embodiment" or combinations and/or variations of these terms means that a particular feature, structure or characteristic described in connection with the embodiment or example is included in at least one embodiment or example of the present disclosure. Thus, the appearances of the phrases "in one example" or "in an example" in various places throughout this specification are not necessarily all referring to the same example embodiment or example. Furthermore, the particular features, structures, or characteristics may be combined in any suitable manner in one or more embodiments or examples.

Definitions

Generally, as used herein, the following terms have the following meanings when used within the context of diagnostic test strips:

The articles "a" or "an" and the phrase "at least one" as used herein refers to one or more.

Dimethyl sulfoxide ("DMSO") is an organosulfur compound with the formula (CH3)2SO.

"HRP" refers to the enzyme horseradish peroxidase, found in the roots of horseradish.

As used herein, "plurality" is understood to mean more than one. For example, a plurality refers to at least two, three, four, five, ten, 25, 50, 75, 100, 1,000, 10,000 or more.

"Obtaining" is understood herein as manufacturing, purchasing, or otherwise coming into possession of.

"TMB" as used herein means 3,3',5,5'-Tetramethylbenzidine that in one form can have the chemical formula C16H20N2.

"Zika virus" has its generally understood meaning as an infectious disease from the virus family Flaviviridae which is spread from the *Aedes* mosquitoes.

EXAMPLE EMBODIMENTS

Referring now to FIG. 1, a process flow diagram of a silk fibroin extraction procedure for making a Zika test strip is schematically illustrated. A silk fibroin extraction procedure[1] for making a Zika test strip 10 the initial act 12 starts the process with obtaining a plurality of *Bombyx mori* silk cocoons 13. The next operation 14 is to cut the plurality of cocoons 15 and dispose of the worm. At step 16 the cocoons are boiled for 30 minutes in 0.02 M $Na_2CO_3$ followed by rinsing fibers 17 at step 18. Next the fibers 17 are squeezed to remove excess water and allowed to dry overnight on a suitable substrate 19. After drying, a solution of 9.3 M LiBr 21 is added on top of the plurality of silk fibers 17 and the fibers in solution are incubated at 60° C. for 4 hours 22. The resultant solution of fibers and LiBr are then transferred to a suitable syringe 23 for adding to a dialysis cassette 25 at step 24. One or more cassettes may then be dialyzed against ultrapure water for about 48 hours at step 26. The silk solution is then removed from the cassette 25, using, for example a new syringe 23, at step 28. The solution is then dispensed into a container, such as test tube 31, and centrifuged twice 30. The centrifuged solution is then stored in the test tube 31 at 4° C. at step 32. Finally, the centrifuged solution is removed from storage and used to coat a paper substrate 41 at step 40. The substrate may then be cut into strips as desired.

To make the test specific to Zika virus, an antibody conjugation to HRP caused a conjugation similarly found in MAC-ELISA tests. In MAC-ELISA tests, an antibody conjugation is used to differentiate between similar antigens and/or proteins. By having TMB and ZVNS1/HRP on opposite ends of the test strip, it will cause the reagents to not react unless the ZVNS1 antigen or protein is present. In MAC-ELISA tests, a pile of reagents is used to cause a reaction.

To make the test strip temperature-independent, different films and biomaterials were researched using journals and literature. Silk fibroin was found to stabilize temperature-dependent reagents and create a film to encase reagents. In one example, Cocoons of *Bombyx mori* silkworm silk, HRP (Type VI-A lyophilized powder), 3,3',5,5'-tetramethylbenzidine (TMB) solutions were used. Lithium Bromide for the fabrication of silk fibroin film was purchased from Sigma-Aldrich. 102 filter paper 2 mm, EZ-Link Peroxidase Conjugation Kit, and Zika Virus NS1 Antibodies were purchased by ThermoFisher. Zika NS1 (ZVNS1), Dengue NS1 (DVNS1), and West Nile NS1 (WNVNS1) proteins were cultured from Human T-Cells and were supplied from MyBioSource and The Gale Laboratory at UW Medicine.

In one example, silk fibroin protein extraction was accomplished using the following method and the materials as listed above:

1. A 1000 mL beaker was filled with 900 mL of distilled water (DI water).
   a. The top of the beaker was covered with aluminum foil and a hot plate was set to high. The beaker was put on the hot plate until the water came to a boil.
2. 2.25 g of sodium carbonate (Na2CO3) was weighed out.
3. 2.5 g of *Bombyx mori* silk worm cocoons was weighed out. When the water was at a boil, the aluminum foil was removed and Na2CO3 and cocoons combined.
4. The cocoons were allowed to boil for 30 mins with occasional stirring.
5. After 30 minutes, the silk fibers were rinsed in DI water for 10 mins 3 times.
   a. Excess water was removed from the silk fibers which were then spread on aluminum foil, allowing them to dry overnight.
6. The dried silk fibers were dispensed into a 50 mL beaker which was then filled with 9.3 M Lithium Bromide (LiBr).
   a. The beaker including the dried silk fibers were incubated in an incubator at 60° C. for 4 hours.
7. After 4 hours, the solution was dialyzed against ultra-pure water for 4 days.
8. After dialysis, the silk fibroin solution was put into a conical and centrifuge.
9. Following the centrifuge step, the solution was stored at 4° C.

Figure 2:
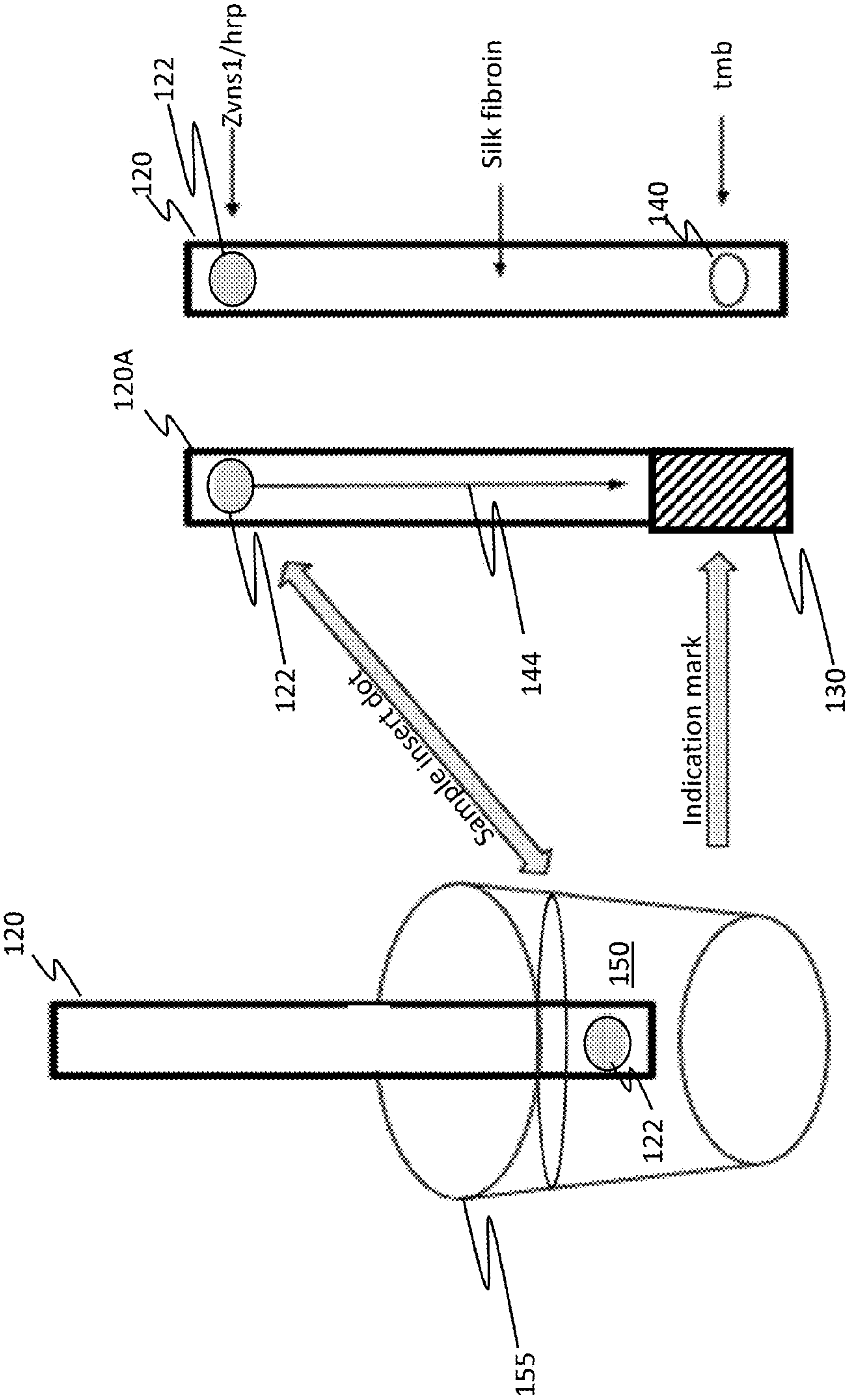
FIG. 2 schematically illustrates an example of using a silk fibroin encasement, such as a paper test strip for detecting Zika Antigen in a sample.

Referring now to FIG. 2, an example of using a silk fibroin encasement, such as a paper test strip for detecting Zika Antigen in a sample is schematically shown. A Zika NS1 paper test strip 120, made according to the method described above with reference to FIG. 1, additionally includes a sample insert dot 122 where the ZVNS1/HRP conjugation was placed. In one example, a sample dot is put on the strip and a ZVNS1/HRP conjugation is applied over the sample dot. In one example the sample dot is colored red. On the opposite end of the strip, where the TMB is applied, is where the indication is placed, also known as the indication mark 130.

As indicated above, MAC-ELISA tests for Zika virus cost around $300-$800 and use Immunoglobin M (IgM) antibody. IgM is the capture antibody and attaches onto the target antigen. MAC-ELISA tests are used for the qualitative detection of diseases using antibodies from patient-matched serum samples. As opposed to expensive MAC-ELISA testing, the new test strip 120, disclosed for the first time herein, costs less than $1 to make and is about 99.9% cheaper to produce versus MAC-ELISA tests for Zika virus.

In known MAC-ELISA tests, a color change will occur using a microplate reader. The paper test strip to detect Zika virus uses technology that is in MAC-ELISA tests, but puts it on a 2D paper network. The test strip delivers a response in under 2 minutes in contrast to MAC-ELISA tests which typically take hours to run and a few days to analyze. As indicated by the patterned indication mark 130, a positive result for Zika virus will result in, for example, a green colorimetric change using Bromophenol Blue on the bottom of the strip. Using an identical test strip, a negative result will make the strip stay blue.

In one example, strip 120A represents a test strip 120 that has been inserted in a sample 150 held in a container 155. Reference arrow 144 indicates the flow of reagents as they move down the strip from the indicator dot 122 to the indication mark 130.

Figure 3:
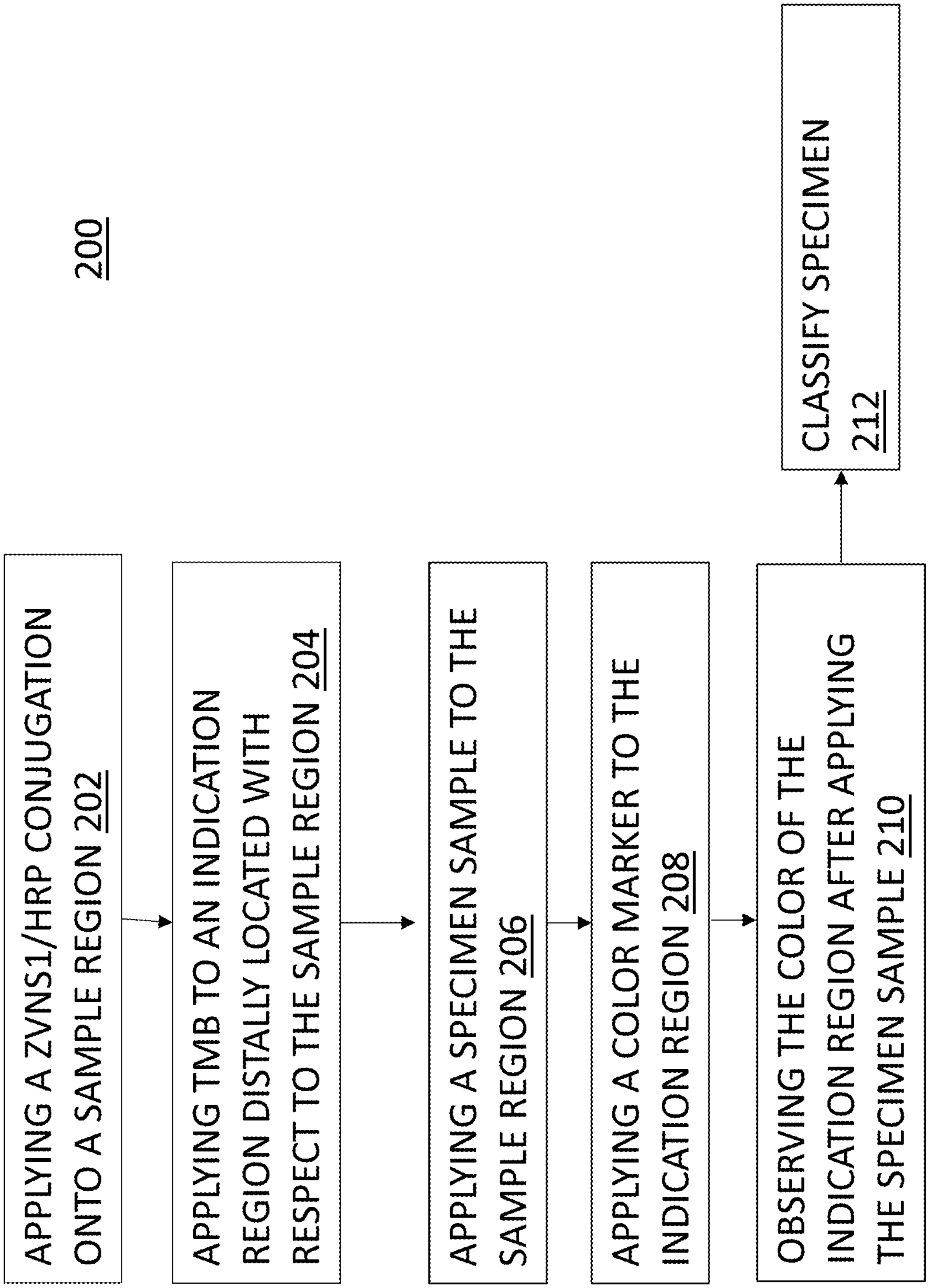
FIG. 3 shows a process flow diagram for detecting the presence of Zika virus.

Referring now to FIG. 3, a process flow diagram for detecting the presence of Zika virus is illustrated. Using a test strip as described hereinabove, the method 200 included the following acts:

applying a ZVNS1/HRP conjugation onto a sample region 202;

applying TMB to an indication region distally located with respect to the sample region 204;

applying a specimen sample to the sample region 206;

then applying a color marker to the indication region 208;

observing the color of the indication region after applying the specimen sample 210; and classifying the specimen sample as positive or negative depending upon the color.

In one example, the act of applying a color marker included applying a pH indicator. The pH indicator may include Bromophenol Blue, or the like, for example, wherein the color green indicates a positive result.

EXAMPLES

During testing, there were two different testing phases to test for the detection of Zika virus and to test if the strip could differentiate between virus types. Phase 1 tests for ZVNS1 detection used biological cross-reactivity with an unrelated protein sample, and non-biological cross-reactivity with a lysate buffer. Phase 2 tests for differentiation between Zika and NS1 protein types used Dengue NS1 (DVNS1) protein and West Nile NS1 (WNVNS1) protein samples.

Zika Antigen Detection via Silk Fibroin Encasement

In one example, Zika Virus NS1 Antibody was conjugated to Horseradish peroxidase (HRP) using the EZ-Link Peroxidase Kit according to the following procedure.

ZVNS1/HRP Conjugation 1. 1 mg of ZVNS1 antibody was added to 1 mL of Phosphate Buffered Saline (PBS).
2. 1 mg of Horseradish peroxidase (HRP) was reconstituted with 100 μL of distilled water.
   a. The ZVNS1 antibody solution was added in a 15 mL conical with the reconstituted HRP solution.
   b. The solution was vortexed for 5 sec.
3. In a fume hood, 10 μL of Sodium Cyanoborohydride was added to the solution and incubated at room temperature for 1 hour.
4. Then, 20 μL of Quenching Buffer was added and kept at room temperature for 15 min.
5. The solution was stored at 4° C.

Subsequently, 3,3'5,5'-Tetramethylbenzidine (TMB) substrate solution was diluted in 1 mL of Dimethyl Sulfoxide (DMSO) and 9 mL of 0.05 M Phosphate Citrate Buffer was added to the solution.

5 μL of TMB substrate solution was pipetted on the left side of the filter paper and 5 μL of the ZVNS1/HRP conjugate solution was pipetted on the right side of the filter paper. The filter paper dried for 10 min until being soaked in silk fibroin solution for 5 sec and dried for 3 hours before use.

Detection of ZVNS1

The following procedure was used in conducting tests for detection of ZVNS1.

A 5 μL of sample was added on the red insert dot on a test strip.

a. Samples used included:
      i. Zika NS1 protein experimental sample.
      ii. Dengue NS1 protein biological control.
      iii. West Nile NS1 protein biological control.
      iv. GFP biological control.
      v. Lysate buffer mock biological control.

2. After a test strip was wetted by the test solution, it was hung vertically for about 1 min and 30 sec.
3. next, 10 μL of Bromophenol Blue was added to the test strip.
   a. A positive sample turned green.
   b. A negative sample turned blue.

Methodology: Prototype #1

In one example, 102 mm filter paper strips were cut into 2×6 mm strips. Using thin paper strips allows for an easy flow-through of reagents to pass through the flow channels in the filter paper. Following, 1 mL of ZVNS1 monoclonal antibody was conjugated to the enzyme Horse Radish Peroxidase (HRP) per EZ-Link HRP Conjugation kit and on the top of the strip, 2×1 mm of the strip was dipped into the ZVNS1/HRP conjugate. On the bottom of the strip, 2×1 mm of the filter paper was dipped into the 3,3'5,5'-Tetramethylbenzidine (TMB) solution. The test strip was then encased with the silk fibroin solution and left to dry for 3 hours.

Methodology: Prototype #2

In another example, 102 mm filter paper strips were cut into 2×6 mm strips. Following, 1 mL of ZVNS1 monoclonal antibody was conjugated to the enzyme Horse Radish Peroxidase (HRP) per EZ-Link HRP Conjugation kit and 5 μL of ZVNS1/NS1 conjugate was pipetted on the top of the strip. 100 μL of Congo Red was diluted in Phosphate Buffered Saline (PBS) was added to a total volume of 2 mL of the ZVNS1/HRP conjugation before being placed on the filter paper. 5 μL of TMB solution was pipetted on the bottom of the strip. By pipetting the reagents instead of dipping, it allows for the reagents to not unintentionally react, reduces the waste of materials, and allows for a controlled amount of reagent. The test strip was then soaked in the silk fibroin solution for 5 seconds and then allowed to dry for 3 hours.

Protein Concentrations

In a study published by Fourcade, viral RNA was isolated from 140 μL samples of Zika infected patients and cell culture supernatant using a RT-PCR (Fourcade, 2016). In plasma, the viral load of ZVNS1 antigens is between 100 copies/mL to 630 copies/mL. In urine, the viral load is between 260 copies/mL to 74,000 copies/mL. To determine the concentration of the protein samples used, the following calculation was made:

$$\frac{250 \text{ copies}}{1 \text{ mL}} \times \frac{1\ IU}{5.6 \text{ copies}} \times \frac{0.00121\ \mu g}{1\ IU} = \frac{0.05\ \mu g}{1 \text{ mL}}$$

By converting from copies/mL to International Units (IU), the conversion to ug/mL could be made. The concentrations used were 0.01 ug/mL to 0.13 ug/mL. The protein calculations were within range of human serum and urine samples.

Discussion & Results

Using an antibody conjugate to HRP, when the virus was present, the reaction between HRP and TMB was activated and produced a colorimetric change using protein dilutions that realistically represent that for human blood serum and urine samples.

In prototype #1, the success rate was 53% due to pipetting the sample in the center of the strip. Originally, the sample was hypothesized to pull the reagents to the center to cause an oxidation reaction to produce a pH change in response to the ZVNS1 protein. By having a low success rate, the test could not accurately nor precisely detect ZVNS1 proteins and/or antigens. The false positive rates were under 17% for prototype #1 which led to a refining in the prototype to create prototype #2.

In prototype #2, the sample was placed on the ZVNS1/HRP conjugate, also known as the sample insert dot, and then hung vertically for 1 to 2 minutes. Following, HRP and TMB reacted and produced a 3.24 pH change in response to ZVNS1 proteins and/or antigens. The overall success rate for the detection of ZVNS1 was 99% and the response time was under 2 minutes. Thus, the test could detect ZVNS1 proteins and/or antigens.

Testing for biological and non-biological cross-reactivity using non-related samples, the false positive rate was under 3% overall. The GFP biological control false positive rate was 1% whereas the mock biological control false positive rate was 3%. This suggests that the test strip has a low false positive rate when introduced to other biological and non-biological agents, suggesting that the strip only reacts to ZVNS1 proteins and/or antigens.

In prototype #2, the overall success rate increased through trials 1 to 7 due to an optimization of the prototype. Limiting TMB's exposure to oxygen and light by aliquoting 100 μL samples of TMB increased the shelf life of the test strip. Using fresh samples of the ZVNS1/HRP conjugate allowed for a longer shelf life of the test strip due to the intrinsic nature of the ZVNS1 antibody. By using fresh samples of the silk fibroin protein, the encasement of the reagents allowed for a better stabilization of the reagents under temperatures as high as 45° C. and humidity of 90%.

During phase 2 of testing for differentiation of NS1 protein types, failure rates were under 4%. The DVNS1 failure rate was 3% whereas the WNVNS1 failure rate was 4% for preliminary trials. With failure rates being low, the test strip was determined to differentiate between protein types, did not react to tested biological agents, and could only detect the ZVNS1 protein.

Because the test strip uses an antibody conjugation, the antibody could be replaced and engineered towards other diseases: Ebola, HIV/AIDS, MERS-COV, Malaria, pancreatic cancer, lung cancer, colon cancer, etc.

Test results are summarized in Table I.

TABLE I

| Trial | Protoype | Success | Fail |
|---|---|---|---|
| 1 | 1 | 53 | 47 |
| 1 | 2 | 85 | 15 |
| 2 | 2 | 88 | 12 |
| 3 | 2 | 91 | 9 |
| 4 | 2 | 97 | 3 |
| 5 | 2 | 98 | 2 |
| 6 | 2 | 97 | 3 |
| 7 | 2 | 99 | 1 |

Each trial in table 1 included a sample size of 100 samples. Success was interpreted as correctly classifying sample as positive or negative. Fallis classified as incorrectly classifying a sample, as for example a false positive or a false negative.

The invention has been described herein in considerable detail in order to comply with the Patent Statutes and to provide those skilled in the art with the information needed to apply the novel principles of the present invention, and to construct and use such exemplary and specialized components as are required. However, it is to be understood that the invention may be carried out by different equipment, and devices, and that various modifications, both as to the equipment details and operating procedures, may be accomplished without departing from the true spirit and scope of the present invention.

REFERENCES

The teachings of the following publication are incorporated herein in their entirety by this reference.

1. BIOTREND Cheikalien GmbH. *General Elisa Kit* [Material Safety Data Sheet]. Kaufman, P. et al., Visualization and Measurement of Flow in Two-dimensional Paper Networks. *Lab Chip.* 2010, 10, No. 19. 2614-2617

2. Centers for Disease Control. (2017). Retrieved from www.cdc.gov

3. Centers for Disease Control. (2017). *Symptoms.* Retrieved from www.cdc.gov

4. Cohen, J. (2016). Science Magazine. *Zika's Long, Strange Trip Into Limelight.* Retrieved from www.sciencemag.org.

5. CNN. (2016). *What We're Doing About The Zika Virus.* Retrieved from www.cnn.com.

6. Lu, Q., Wang, X., Hu, X., Cebe, P., Omenetto, F. and Kaplan, D. L. (2010), Stabilization and Release of Enzymes from Silk Films. Macromol. Biosci., 10: 359-368. doi: 10.1002/mabi.200900388.

7. New York Times. (2016). *Want a Zika Test? It's Not So Easy.* Retrieved from www.nytimes.com.

8. Rockwood, Danielle N., Preda, Rucsanda C., Yucel, T., Wang, X., Lovett, M., & Kaplan, D. L., Materials Fabrication from *Bombyx mori* silk fibroin. *Nature Protocols.* 2011, Vol 6, No. 10. 1612-1631.

9. World Health Organization. (2017). Retrieved from www.who.int.

10. Vepari, C. & Kaplan, D. L. Silk as a biomaterial. *Prog. Poly. Sci.* 2007, 32, 991-1007.

11. Viral load kinetics of Zika virus in plasma, urine and saliva in a couple returning from Martinique, French West Indies. Fourcade, Camille et al. Journal of Clinical Virology, Volume 82, 1-4.

What is claimed is:

1. A method for making a paper test strip for detecting Zika antibodies indicating the presence of Zika virus in a sample, the method comprising:

obtaining a plurality of *Bombyx mori* silk worm cocoons;

mixing the plurality of *Bombyx mori* silk worm cocoons with Na2CO3 in water;

boiling the mixture for predetermined time to combine the cocoons and Na2CO3 into a plurality of silk fibroin fibers;

rinsing the silk fibroin fibers in distilled water;

removing excess water from the rinsed silk fibroin fibers;

drying the silk fibroin fibers;

dispensing the silk fibroin fibers into a container with Lithium Bromide (LiBr) to form a silk fibroin solution;

incubating the silk fibroin solution in the container;

dialyzing the silk fibroin solution in water;

centrifuging the silk fibroin solution;

storing the silk fibroin solution at 4° C.;

then coating at least one 2D matrix of filter paper in the silk fibroin solution to encase the fibroin solution;

allowing the at least one 2D matrix to air-dry;

applying a ZVNS1 anti-Zika monoclonal antibody/Horse Radish Peroxidase (ZVNS1/HRP) conjugation onto a sample region on said filter paper; and applying 3,3'5,5'-Tetramethylbenzidine (TMB) to an indication region distally located with respect to the sample region.

2. The method of claim 1 wherein the silk fibroin solution is 6% w/v.

3. The method of claim 1 wherein the step of coating comprises coating at least one 2 mm strip of filter paper in the silk fibroin solution for 10 seconds and hanging the at least one 2 mm strip vertically to air-dry for 20 minutes.

4. A Zika virus test strip made in accordance with the method of claim 1.

5. The method of claim 1 wherein the at least one 2D matrix of filter paper comprises a test strip of 102 mm filter having a width and length of at least 2×6 mm.

6. The method of claim 5 further comprising:

conjugating 1 mL of ZVNS1 anti-Zika monoclonal antibody to the enzyme Horse Radish Peroxidase (HRP) on the top of the test strip;

dipping a top 2×1 mm end of the test strip into the ZVNS1/HRP conjugate;

dipping a bottom 2×1 mm of the test strip into the 3,3'5,5'-Tetramethylbenzidine solution;

encasing the test strip with the silk fibroin solution; and drying the test strip for 3 hours.

7. The method of claim 5 further comprising:

conjugating 1 mL of ZVNS1 anti-Zika monoclonal antibody to the enzyme Horse Radish Peroxidase (HRP) and pipetting 5 μL of ZVNS1/HRP conjugate on the top of the strip;

diluting 100 μL of Congo Red in Phosphate Buffered Saline (PBS) and adding it to a total volume of 2 mL of the ZVNS1/HRP conjugation before applying to the filter paper;

pipetting 5 μL of TMB solution on the bottom of the test strip;

soaking the test strip was in the silk fibroin solution for 5 seconds; and then allowing the test strip to dry.

8. A method for detecting the presence of Zika antibodies indicating the presence of Zika virus in a patient sample comprising:

obtaining a plurality of *Bombyx mori* silk worm cocoons;

mixing the plurality of *Bombyx mori* silk worm cocoons with Na2CO3 in water;

boiling the mixture for predetermined time to combine the cocoons and Na2CO3 into a plurality of silk fibroin fibers;

rinsing the silk fibroin fibers in distilled water;

removing excess water from the rinsed silk fibroin fibers;

drying the silk fibroin fibers; dispensing the silk fibroin fibers into a container with Lithium Bromide (LiBr) to form a silk fibroin solution;

incubating the silk fibroin solution in the container; dialyzing the silk fibroin solution in water;

centrifuging the silk fibroin solution;

storing the silk fibroin solution at a predetermined temperature;

then coating at least one 2D matrix of filter paper in the silk fibroin solution to encase the fibroin solution;

allowing the at least one 2D matrix to air-dry;

applying a ZVNS1 anti-Zika monoclonal antibody/Horse Radish Peroxidase (ZVNS1/HRP) conjugation onto a sample region on said filter paper;

applying 3,3'5,5'-Tetramethylbenzidine (TMB) to an indication region distally located with respect to the sample region;

applying a specimen sample from the patient to the sample region;

then applying a color marker to the indication region;

observing the color of the indication region after applying the specimen sample; and classifying the specimen sample as positive or negative depending upon the color.

9. The method of claim 8 wherein the act of applying a color marker comprises applying a pH indicator.

10. The method of claim 8 wherein the pH indicator comprises Bromophenol Blue.

11. The method of claim 8 wherein the color green indicates a positive result.

12. A paper test strip for indicating the presence of Zika virus in a patient sample using an enzyme solution, the paper test strip comprising:

where the enzyme solution consists of 1 mg of ZVNS1 antibody added to 1 mL of Phosphate Buffered Saline (PBS), 1 mg of Horseradish peroxidase (HRP) reconstituted with 100 μL of distilled water, where the ZVNS1 antibody solution was added in a 15 mL conical with the reconstituted HRP solution to create a ZVNS1/HRP solution and the ZVNS1/HRP solution is vortexed for 5 sec., 10 μL of Sodium Cyanoborohydride added to the ZVNS1/HRP solution and incubated at room temperature for 1 hour, 20 μL of Quenching Buffer added to the incubated solution and kept at room temperature for 15 min, after storing the solution at 4° C., then a substrate of 3,3'5,5'-Tetramethylbenzidine (TMB) substrate solution diluted in 1 mL of Dimethyl Sulfoxide (DMSO) and 9 mL of 0.05 M Phosphate Citrate Buffer is added to the solution;

a 2D matrix of filter paper; and a *Bombyx mori* silk worm cocoon fibroin solution applied to the 2D matrix of filter paper of filter paper wherein the *Bombyx mori* silk worm cocoon fibroin solution is mixed with the enzyme solution in phosphate buffered saline buffer.

13. The paper test matrix of claim 12 wherein the *Bombyx mori* silk worm cocoon fibroin solution is 6% w/v.

14. The paper test strip of claim 12 wherein the test strip includes the 2D matrix of filter paper configured into a strip of 102 mm filter having a width and length of at least 2×6 mm;

wherein the silk fibroin solution includes 1 mL of ZVNS1 anti-Zika monoclonal antibody conjugated to the enzyme Horse Radish Peroxidase (HRP) and applied over the strip, wherein a top 2×1 mm end of the test strip is dipped into the ZVNS1/HRP conjugate;

a bottom 2×1 mm of the test strip is dipped into the 3,3'5,5'-Tetramethylbenzidine solution; and the test strip is encased with the silk fibroin solution and dried for 3 hours.

15. The paper test matrix of claim 12 wherein 1 mL of ZVNS1 anti-Zika monoclonal antibody is conjugated to enzyme Horse Radish Peroxidase (HRP) and 5 μL of ZVNS1/HRP conjugate is pipetted on the top of the strip;

100 μL of Congo Red as diluted in Phosphate Buffered Saline (PBS) and added to a total volume of 2 mL of the ZVNS1/HRP conjugation before applying to the filter paper;

5 μL of TMB solution is pipetted onto the bottom of the strip; and the test strip is soaked in the silk fibroin solution for 5 seconds and then allowed to dry.

* * * * *